(12) United States Patent
Herrmann

(10) Patent No.: US 8,426,819 B2
(45) Date of Patent: Apr. 23, 2013

(54) METHOD FOR THE NON-INVASIVE OPTIC DETERMINATION OF THE TEMPERATURE OF A MEDIUM

(75) Inventor: Vera Herrmann, Luebeck (DE)

(73) Assignee: Nirlus Engineering AG, Luebeck (DE)

( * ) Notice: Subject to any disclaimer, the term of this patent is extended or adjusted under 35 U.S.C. 154(b) by 0 days.

(21) Appl. No.: 12/812,992

(22) PCT Filed: Jan. 23, 2009

(86) PCT No.: PCT/EP2009/000440
§ 371 (c)(1),
(2), (4) Date: Nov. 17, 2010

(87) PCT Pub. No.: WO2009/092603
PCT Pub. Date: Jul. 30, 2009

(65) Prior Publication Data
US 2011/0108730 A1   May 12, 2011

(30) Foreign Application Priority Data

Jan. 25, 2008   (DE) .................... 10 2008 006 245

(51) Int. Cl.
*G01J 5/58* (2006.01)
(52) U.S. Cl.
USPC .................................................. 250/339.04
(58) Field of Classification Search ............. 250/339.04
See application file for complete search history.

(56) References Cited

U.S. PATENT DOCUMENTS

| | | | |
|---|---|---|---|
| 5,455,177 A | 10/1995 | Krause | |
| 5,876,121 A * | 3/1999 | Burns et al. | 374/161 |
| 7,077,565 B2 | 7/2006 | Pesach | |
| 7,251,518 B2 | 7/2007 | Herrmann | |
| 2004/0099815 A1 * | 5/2004 | Sfez et al. | 250/492.1 |

FOREIGN PATENT DOCUMENTS

| | | |
|---|---|---|
| DE | 10348958 B | 5/2005 |
| DE | 102006036920 B | 11/2007 |

OTHER PUBLICATIONS

Hollis, Veronica "Noninvasive monitoring of brain tissue temperature . . . " www.medphys.uc XP 002541690, 2003.
Norris, K.H. "Possible medical applications of NIR".

* cited by examiner

*Primary Examiner* — Marcus Taningco
(74) *Attorney, Agent, or Firm* — Andrew Wilford

(57) ABSTRACT

Disclosed is a method for the non-invasive optic determination of the temperature of a medium, preferably a water-containing medium, wherein the medium to be analyzed is illuminated by infrared and/or visible light in the region of an absorption line, the position of which depends on the temperature of the medium, and wherein absorption of the light in the region of the absorption line is measured and the temperature is determined from said measurement by comparison with calibration data. Said method is characterized in that the medium is illuminated with at least two discrete light wavelengths ($\lambda_1, \lambda_2$), which are in the region of the absorption line (B) on different sides of the absorption maximum, that at least one measured value ($\Delta A/\Delta \lambda$) dependent on temperature is determined from the relationship of these two determined absorption values to one another, and that the temperature is determined from said measured value by comparison with the previously recorded calibration data.

8 Claims, 5 Drawing Sheets

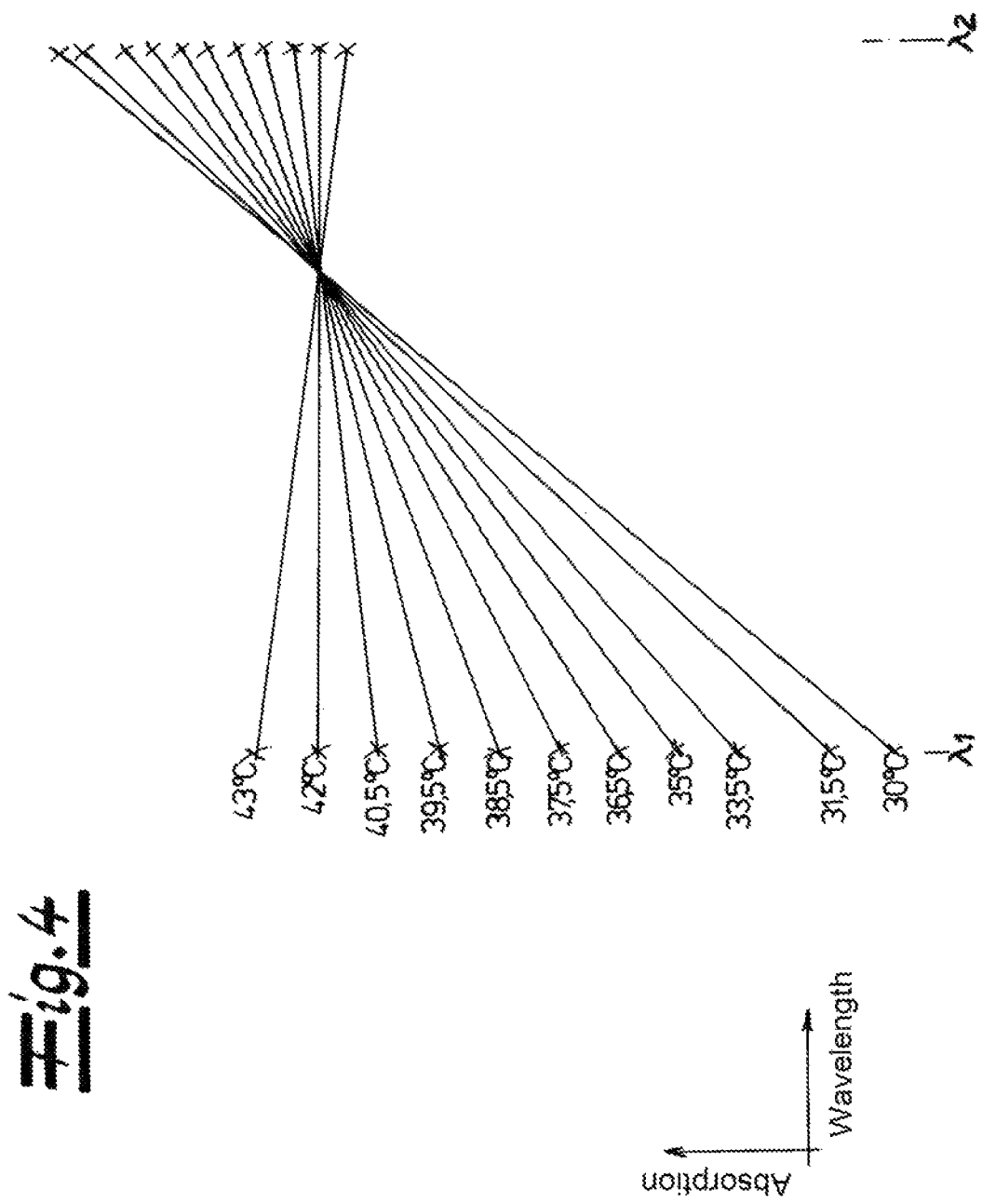

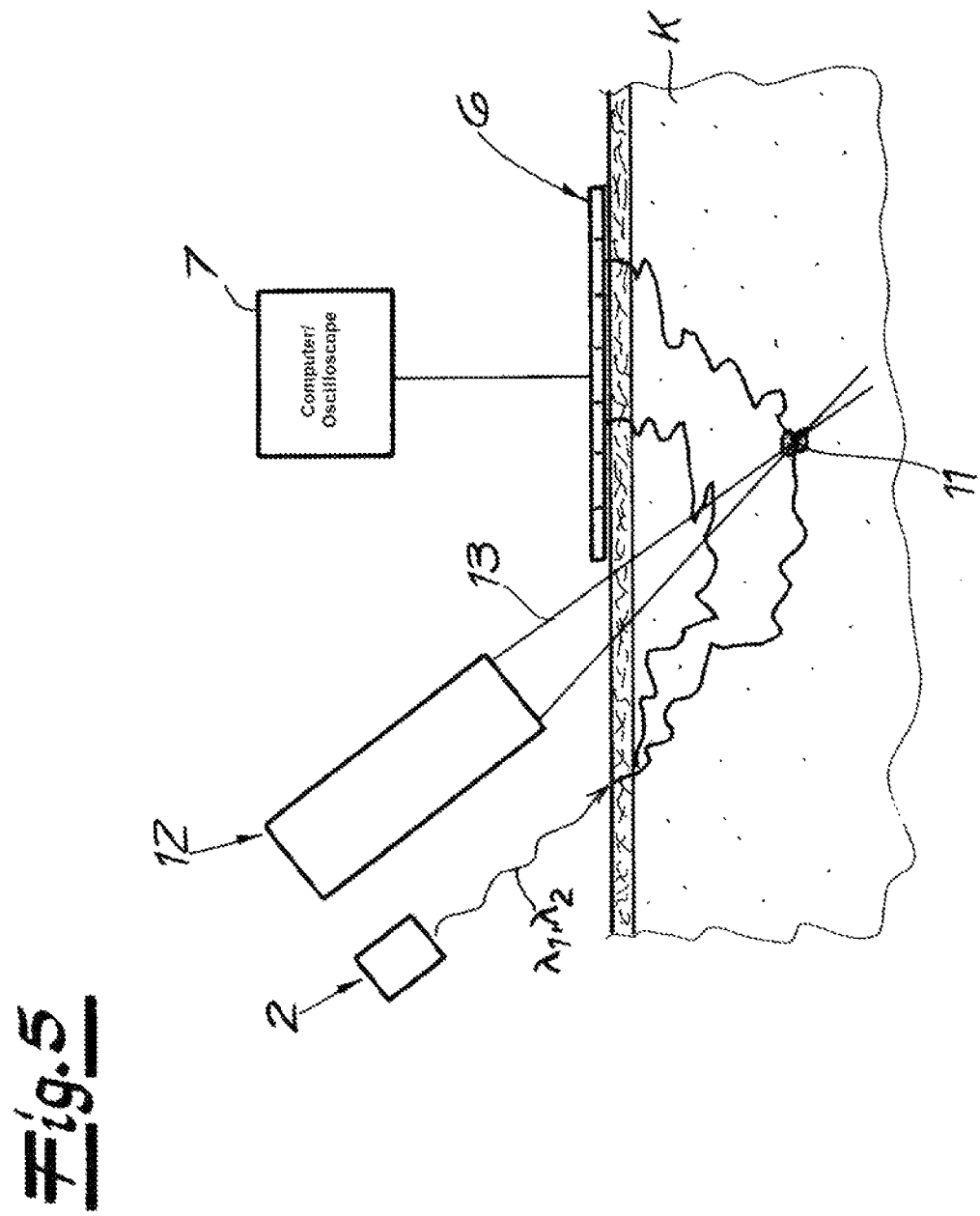

METHOD FOR THE NON-INVASIVE OPTIC DETERMINATION OF THE TEMPERATURE OF A MEDIUM

CROSS REFERENCE TO RELATED APPLICATIONS

This application is the US national phase of PCT application PCT/EP2009/000440, filed 23 Jan. 2009, published 30 Jul. 2009 as WO2009/092603, and claiming the priority of German patent application 102008006245.6 itself filed 25 Jan. 2008, whose entire disclosures are herewith incorporated by reference.

BACKGROUND OF THE INVENTION

The invention relates to a method of the noninvasive optical determination of the temperature of a medium, preferably a water-containing medium, where the medium to be analyzed is irradiated by infrared and/or visible light near an absorption line whose position depends on the temperature of the medium, and where the absorption of the light is measured near the absorption line and the temperature is determined from the measurement by comparison with calibration data. Medium in the context of the invention means in particular a water-containing medium, for example living tissue, and in particular (flowing) blood within the human body. Absorption in the context of the invention means, on the one hand, the absorption behavior measured, for example in transmission, but, on the other hand, also the backscatter behavior dependent on the absorption.

The determination of the temperature, for example of a human body, plays an important role in a variety of areas in medicine, for example during temperature monitoring of intensive-care patients. In practice, the noninvasive measurement of the body temperature by ear thermometers is frequently used, where this kind of measurement is limited to the "discrete" use, that is the measurement at regular intervals. To date, for a continuous temperature monitoring, invasive measuring methods are used in practice where probes or catheters are inserted or placed into the body.

Moreover, in connection with the noninvasive measurement of the concentration of blood components and in particular in connection with the measurement of the glucose concentration in flowing or pulsating blood, there is the need of temperature determination "in situ" because such measurements using calibration curves are usually dependent on the temperature (see DE 10 2006 036 920 and DE 103 11 408 [U.S. Pat. No. 7,251,518]). Here, different optical methods of the near infrared spectroscopy (NIRS) are known that, in a noninvasive manner by absorption changes of light in the infrared wavelength range, allow the measurement of the concentration of blood components and, for example, the measurement of the glucose concentration. The important fact is that the living tissue is substantially transparent in the red and infrared range for electromagnetic radiation so that it is possible to "look," within this "biological window" into the tissue at depths of several millimeters up to several centimeters. With, for example, ultrasonic radiation, the target tissue can be localized in such a manner that optical absorption measurements in the localized tissue can be carried out to relatively great depth of the body (see DE 103 11 408 B3 and DE 10 2006 036 920).

Here, it should be noted that in the range of the so-called biological window, "discrete" water absorption bands are present that in the above described measurements of concentration of blood components are usually avoided. However, it is known that the position (and consequently the wavelength) of the absorption maxima and also the height of the absorption line (and consequently the extent and rate of absorption) depend on the temperature of the medium, for example water. For this reason, it has already been proposed to utilize the temperature dependency of the absorption in the range of the water absorption bands to determine the temperature of the water-containing medium. For this purpose it has been proposed to record the shifting of the absorption line spectroscopically (see K. H. Norris, Beltsville, Md. 20705, USA "Possible medical applications of NIR"). However, this known method is comparatively complicated because a complete spectrum always has to be recorded and consequently a "wavelength scan" is performed. Apart from that, the line shifting is relatively small so that very high spectrometer resolutions are required.

A similar method is known from US 2005/0083992 [U.S. Pat. No. 7,077,565]. There, the temperature dependency of the water absorption line is used for temperature determination at a wavelength of approximately 1450 nm. Also, in this known method, generally speaking, complete spectra are recorded over a comparatively large wavelength range, that is the complete measurement of the absorption line is carried out as well as the comparison with appropriate calibration data.

OBJECT OF THE INVENTION

Against the background of the known prior art, the object of invention is to provide a method of noninvasive optical determination of the temperature of a medium, preferably a water-containing medium, that allows an exact determination of the temperature of a medium in a simple and noninvasive manner. The method is to be suitable in particular for measuring the temperature inside a body, for example for measuring the temperature of tissue or flowing blood inside a body. Moreover, the method is to be combinable in an advantageous manner with the known methods for the noninvasive determination of the concentration of blood components, for example the measurement of the glucose concentration in pulsating blood.

SUMMARY OF THE INVENTION

To attain this object, the invention teaches for a generic method of noninvasive, optical determination of the temperature of a medium, preferably water-containing medium, of the above described type where the medium is irradiated with (at least) two discrete light wavelengths that are near the absorption line on different sides of the absorption maximum, that at least one measured value dependent on temperature is determined from the relationship of these two determined absorption values to one another, and that the temperature is determined from the measured value by comparison with the previously recorded calibration data. The "ratio" of the two determined absorption values is to be understood as a predetermined "relation" that is to be applied to the two measured values. Particularly preferred meant is here the determination of the difference between the two absorption values that lie on both sides of the maximum.

To begin with, the invention is based on the (known) discovery that within the range of the biological window, a plurality of absorption lines of the water are present, whose heights and also positions (or wavelength) depend in a sensitive manner on the temperature of the water-containing medium. However, in the context of the invention it is not necessary to completely measure the absorption line and/or to exactly determine the position of the absorption maximum. In fact, in the context of the invention, a measurement is carried out in a simple manner with at least two and preferably only two discrete light wavelengths that which lie on opposite sides of the absorption maximum. The invention has recognized that upon a temperature change, the absorption values on both sides of the maximum change significantly in a different manner due to the shifting of the absorption maximum so that—when, for example, the difference of these two values is being determined—this difference depends in a particularly sensitive manner on the temperature of the medium. In other words, during evaluation it is possible to draw a straight line through the two absorption points of the two predefined wavelengths, and as measured value, for example the slope of the straight line is determined, in which slope the difference of these two absorption values is considered. The slope of the straight line and in particular the algebraic sign of the slope depend in a very sensitive manner on the temperature so that an exact temperature determination is also possible without exact determination of the maximum shifting. It is only necessary to measure two absorption values for two predefined wavelengths and to evaluate them in the described manner. This is further clarified hereinafter in the description of the figures. It is needless to say that during temperature determination, after or during determination of the absorption values and the measured values obtained therefrom, a comparison with recorded calibration data is carried out. In this manner, adequate measurements can be carried in the laboratory at known temperatures and the known difference values or slopes can be stored as calibration data so that they can be considered automatically during the measurement. However, it is to be noted that the described "formation of the difference" or determination of the slope involves a preferred embodiment of the evaluation taking into account the two absorption values that flank the maximum. The invention comprises principally other "relations" in which two or even more measured values are considered that lie on both sides of the absorption maximum.

Preferably, the measurement according to the invention is carried out with infrared and/or visible light with a wavelength between 600 and 2500 nm, preferably 800 to 1600 nm. Tests have shown that the measurement of the temperature with infrared light in the range of the water absorption band at about 970 nm achieves excellent results. In this case, at least one wavelength is used between, for example 950 and 970 nm, and at least one wavelength between, for example 975 and 1000 nm. However, it is also possible to work with other water absorption bands within the biological window, for example in the range of the water absorption band at about 1450 nm. Basically, any absorption line can be considered whose the position (wavelength of the maximum) is dependent on the temperature. The optimal range for the measurement, that is the two optimal wavelengths to be used, can be found in practice by experiments. It is always required to select one wavelength below and one wavelength above the absorption maximum. Care must be taken that the distance from the maximum is sufficiently large that in fact the observed effect takes place of the absorption values changing on a temperature change with opposite algebraic sign, that is become greater on one side of the maximum and smaller on the other side. During a temperature increase, the absorption for one of the wavelengths should always increases and for the other wavelength always decreases. During a temperature drop, the opposite behavior should occur. However, the distance of the selected wavelength must not be too far away from the absorption maximum because there is the risk of superposition with other lines or effects. It has proven to be advantageous to define first a certain temperature range, for example 30° C. to 43° C., and then a mean (typical) temperature (for example 37° C.), and to determine there the absorption maximum. The selected wavelengths $\lambda_1$, $\lambda_2$ for the measurement should then be, for example approximately 5 to 30 nm, preferably 5 to 15 nm, above or below the wavelength $\lambda_0$, respectively. This applies in particular for the region of the absorption line at 970 nm. In the case of the absorption line at about 1450 nm, it is possible to measure with a larger distance to the maximum, if applicable.

With the method according to the invention, first of all, it is possible to carry out the temperature measurement of liquids at a defined location, for example in the laboratory or outside of a body without the occurrence of disturbing effects. However, of particular importance is the fact that the method according to the invention is in particular also suitable to measure the temperature on or in a living body "in situ." In particular, the measurement works also in rather deep areas, for example the temperature of flowing blood can be measured in blood vessels in a body. For this, the invention proposes marking the site at which the temperature measurement is to be carried out by appropriate measures. This can be done, for example, by ultrasonic radiation as described, for example, in DE 103 11 408 B3 and DE 10 2006 036 920. The tissue to be examined or the blood vessel can be "marked" with ultrasonic radiation by focusing (pulsed) ultrasonic radiation on the site or the blood vessel. During measurement of the absorption (or backscatter) of the light for the temperature measurement, only the portions of the light incident in the detector are considered that are temporally related to the ultrasonic radiation so that an optical measurement and consequently a temperature determination can be carried in a systematic manner in a low-lying area of a body.

To take account of the fact that, for example the light portion marked by ultrasonic radiation does not solely depend on the temperature of the monitored site but also on the temperature difference between the body surface and the site to be monitored, the invention recommends in a preferred development that first a measurement on the surface of the body takes place. The reference measurement can also be carried out in the manner according to the invention, where here too a marking by ultrasonic focus can be useful. However, it is also possible to perform a conventional reference measurement, for example with a temperature sensor. On the surface, the intensity of the light backscattered from the surface depends only on the temperature of the surface because the light does not have to pass through further intermediate positions. This way, the temperature on the surface is clearly determined. Subsequently, the measurement inside the body can take place, where then the temperature difference or the temperature gradient with respect to the temperature on the surface of the body is determined. The measurement on the surface of the body thus forms a reference measurement to eliminate the potential dependency of the temperature gradient during the subsequent measurement inside the body.

Apart from that it can be helpful to consider an influence on the spectroscopic measurement on human tissue by different factors, for example skin color, skin moisture, thickness and structure of the intermediate tissue sections, hematocrit values (that can vary from person to person), and fat level in the blood that changes hourly in the blood. For this reason it can be useful, in addition to the described absorption measurement and, if appropriate, to the reference measurement to carry out a correction measurement on the body surface, by means of which correction measurement, the described effects and in particular scatter effects on the intermediate positions can be eliminated. For this purpose it is useful to irradiate light with a so-called "isosbestic wavelength" into the body, for example into the tissue and to measure the absorption or the backscatter. Such an isosbestic wavelength is characterized in that the absorption or backscatter depends solely on the different scatter effects in the intermediate positions and not on the absorption behavior of the medium, for example water. With such a measurement at an isosbestic wavelength, therefore, the absorption-independent scatter effects can be compensated or filtered out so that overall a particularly exact measurement works also in low lying layers of a body. In the case of a water-containing medium, for example, an isosbestic wavelength of approximately 808 nm can be used.

Overall, with the method according to the invention, the temperature of a medium can be determined in a simple and particularly exact manner (for example with a precision of ±0.01° C.). Also, the temperature on body surfaces or, particularly preferred, the temperature inside a body can be determined, namely in a noninvasive and optical manner. Also, these measures allow, for example an exact determination of the concentration of blood components and in particular of the glucose concentration in blood because in the course of a known measurement of the concentration (simultaneously), also a noninvasive measurement of the temperature can take place, namely exactly at the site where the concentration is determined. However, the method according to the invention can also be used advantageously in other areas, for example for temperature monitoring of intensive care patients and for temperature monitoring during cryotherapy and medical tumor therapy. Further, temperature monitoring of neonates or also temperature monitoring of persons working in environments exposed to heat can be carried out. Further applications are temperature monitoring in the field of sleep diagnostics, during dialysis, or temperature monitoring of athletes. Also, temperature measurement in industrial applications, for example the determination of heat distribution in the clothing industry is a potential application.

BRIEF DESCRIPTION OF THE DRAWING

Hereinafter, the invention is explained in more detail by means of a drawing illustrating only one embodiment. Therein:

FIG. 4 shows calibration data for a measurement according to FIG. 3, and FIG. 5 is a schematic illustration of the method of the determination of the temperature inside a body.

DETAILED DESCRIPTION

Figure 1:
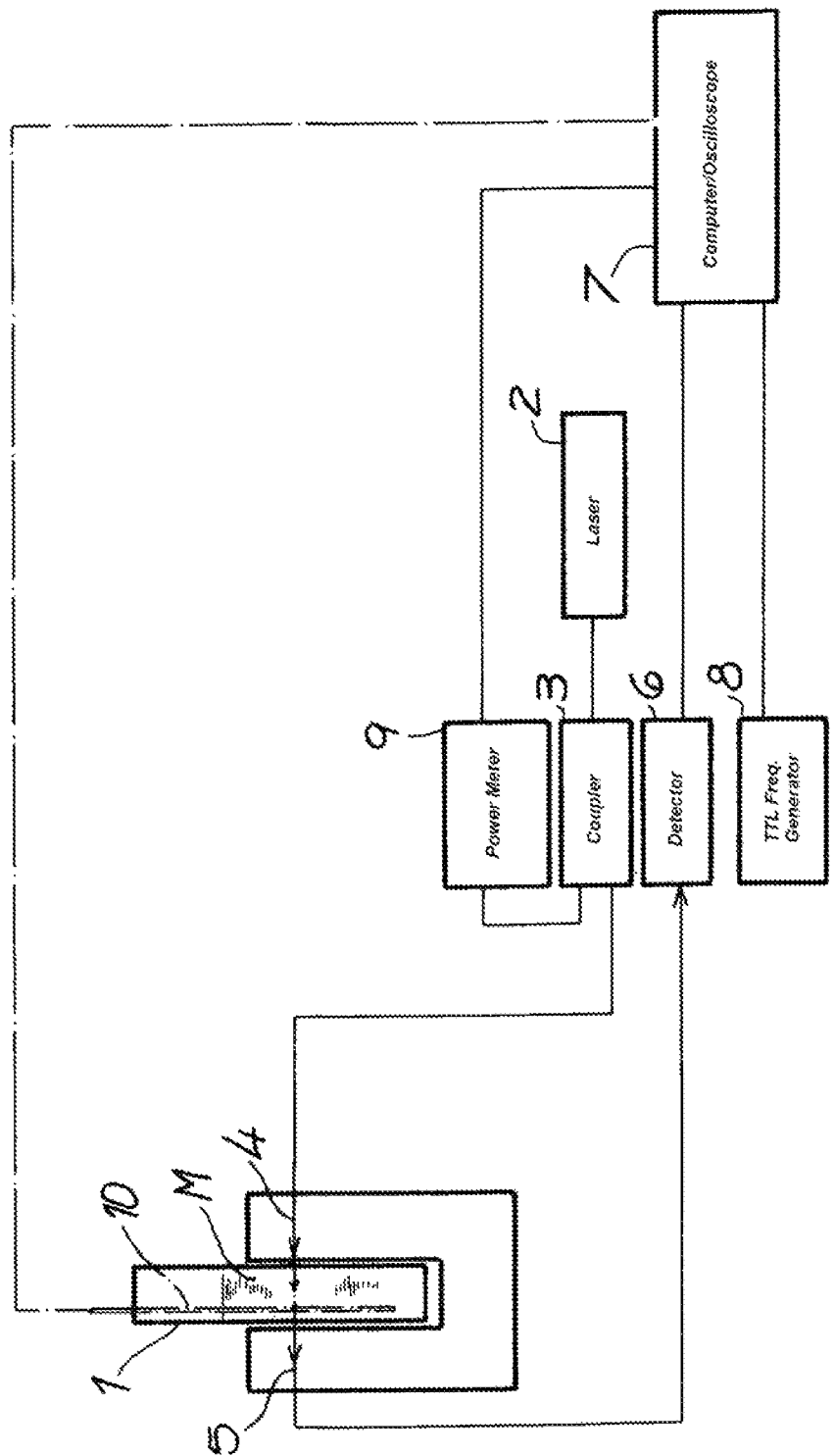
FIG. 1 shows a test set-up for carrying out the method according to the invention, FIG. 2 schematically shows a water-absorption spectrum in a wavelength range of approximately 660 nm to approximately 2400 nm, FIG. 3 schematically shows the water absorption in the range of a water absorption band at about 970 nm at two different temperatures.

In FIG. 1, a test set-up for the determination of the temperature T of a water-containing medium in an optical manner is shown. With this set-up, optical-absorption spectra on a water-containing medium M can be determined. In this laboratory set-up, a water-containing medium M is in a container 1. A tunable infrared laser 2 projects laser light of the desired wavelength via a coupler 3 and an input optical fiber 4 into the medium M. Light exiting the opposite side of the container 1 is decoupled via an output optical fiber 5 and sent to a detector 6. The detector 6 is connected with an evaluation unit 7 that can comprise a computer and/or an oscilloscope. The computer holds the described evaluation algorithm that will be discussed hereinafter in more detail. Also, if applicable, the previously determined calibration data are stored in the computer that can also be considered for the evaluation. This will also be discussed later. A TTL frequency generator 8 is connected to the trigger input of the oscilloscope. Further, a power meter 9 is provided that is also connected, on the one hand, with the computer 7 and, on the other, with the coupler 3. For proving the functional capability of the method according to the invention and, for example also for recording calibration data, a thermometer 10 is shown in FIG. 1 that measures the actual temperature of the water-containing medium exactly so that the temperature data obtained in the manner according to the invention can be verified. It should be noted here that this involves a schematic indication of a laboratory set-up that serves primarily as proof for the functional capability of the method according to the invention. In practice, the optical determination of the temperature T takes place in a similar manner by irradiating laser light into the body. However, in this case it is useful not to measure light in transmission—as in the laboratory—but to measure backscattered light, where the backscattered portion indicates the absorption behavior of the medium. The invention comprises in any case the measurement in transmission as well as in backscatter direction.

Figure 2:
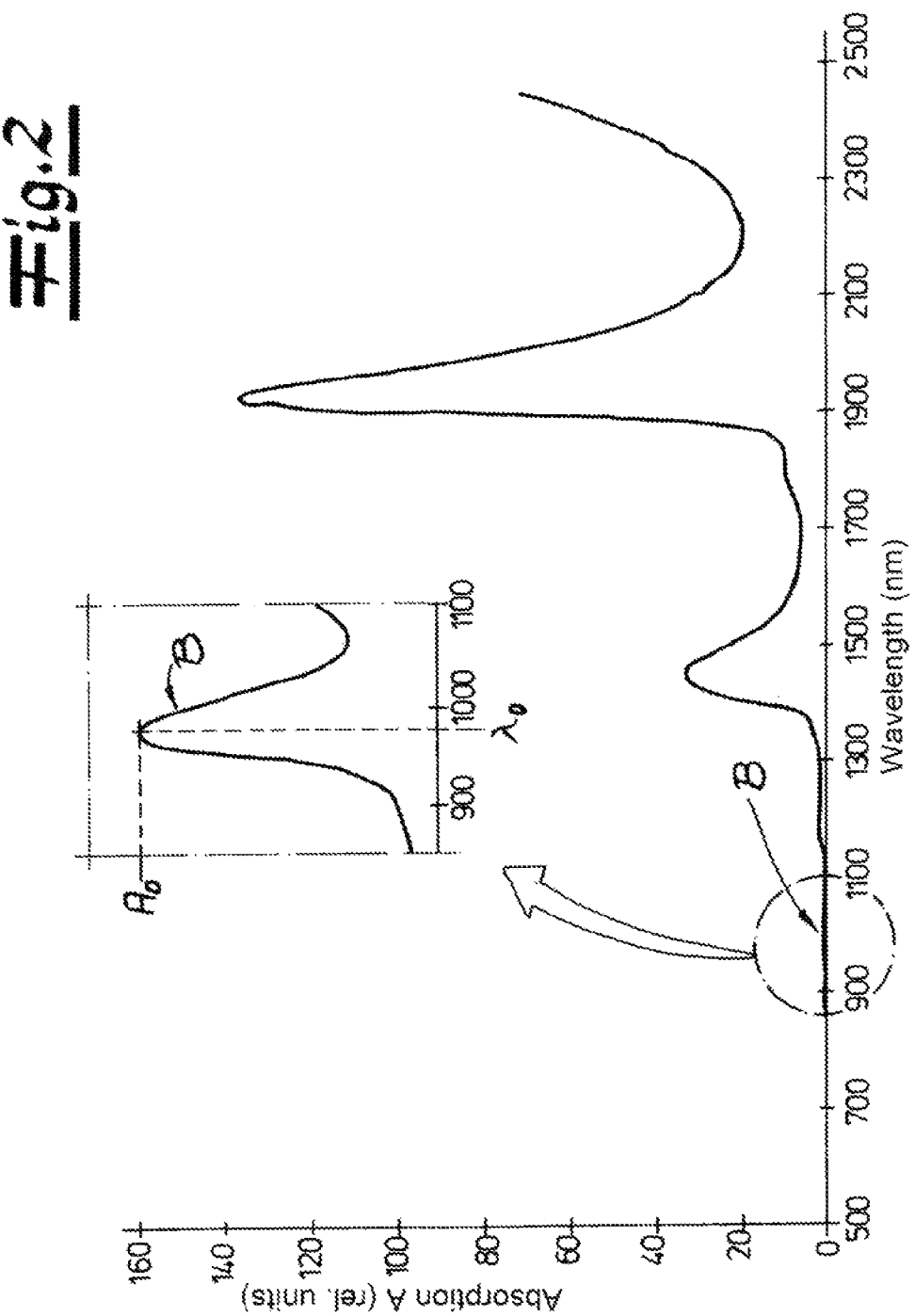
Figure 3:
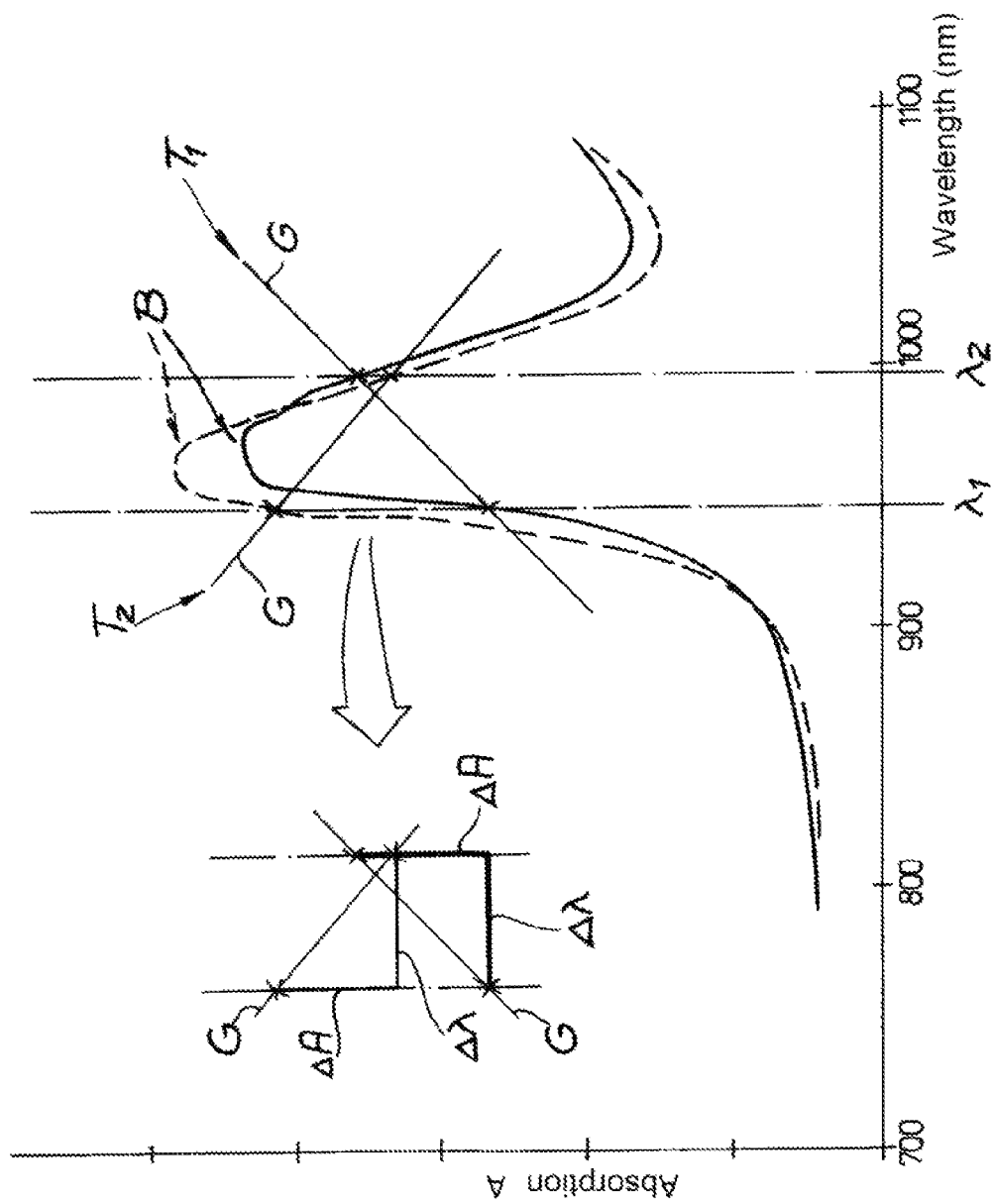

The physical relationships and the operating mode of the method according to the invention are shown in FIGS. 2 to 4.

FIG. 2 shows by way of example and only schematically in an overview a standard absorption spectrum of water in a wavelength range of approximately 700 nm to 2400 nm. The water absorption band B in the range of a wave length of $\lambda_0 \approx 970$ nm is shown. As explained in the description, the position $\lambda_0$ as well as the height $A_0$ of the absorption line B depend on the temperature T of the water. Therefore, $\lambda_0$ represents the wavelength of the absorption maximum at a certain temperature, that is $\lambda_0$ is temperature-independent. As an example, reference is made to FIG. 3 that shows the absorption A near the absorption line B for two different temperatures $T_1=33°$ C. and $T_2=43°$ C. This shows that the absorption line B shifts at higher temperatures toward shorter wavelengths. In the context of the invention, absorption is now measured near the absorption line B, namely only for two predefined wavelengths $\lambda_1$ and $\lambda_2$ that are on different sides of the absorption maximum ($A_0$, $\lambda_0$). These wavelengths are also plotted in FIG. 3. It should be noted that the position of the maximum and therefore $\lambda_0$ itself is temperature-independent. The wavelengths $\lambda_1$ and $\lambda_2$ are to be selected taking into account the selected temperature range in such a manner that, for all temperatures of the range, they are always on different sides of the (shifting) maximum. It is apparent from FIG. 3 that in the range of the wavelength $\lambda_1$, the absorption for the higher temperature $T_2$ is significantly greater than for the temperature $T_1$. This is different on the other side of the absorption maximum $\lambda_0$. There, the absorption for the higher temperature $T_2$ is lower than for temperature $T_1$. This effect can be made clearer by drawing a straight line G through the two measuring points at a temperature T. FIG. 3 shows that the slope $\Delta A/\Delta\lambda$ of the straight line G depends greatly on the temperature T of the medium. This applies equally to the difference $\Delta A$ between the absorption values at a certain temperature $T_1$ or $T_2$ for the two wavelengths $\lambda_1$ and $\lambda_2$ because this difference $\Delta A = A(\lambda_1) - A(\lambda_2)$ determines the slope of the plotted straight line G. In the context of the invention, subsequently, infrared light is irradiated at a certain temperature, namely only two discrete wavelengths $\lambda_1$, $\lambda_2$, flanking the absorption maximum $\lambda_0$. The measured absorption values are set in a relationship, for example as in the shown embodiment, are subtracted from one another, where the formed difference forms the determined measured value that depends greatly on the temperature. The measured value that, in the illustrated embodiment, represents the difference of the absorption values or the slope of the plotted straight line G through the two measuring points is compared with previously recorded calibration data. The calibration data are shown in FIG. 4 for a plurality of temperatures. There, each of the absorption values is plotted for different temperatures at the wavelengths $\lambda_1$ and $\lambda_2$. Further, for illustration purposes, straight lines were drawn through the points that each are assigned to one another in pairs. FIG. 4 shows particularly clearly that the difference between the measured values and therefore also the slope depends greatly on the temperature because increasing or decreasing temperature can in particular cause a sign change. Therefore, at an unknown temperature, the measurement is carried out according to FIG. 2 at the two wavelengths $\lambda_1$ and $\lambda_2$ and subsequently, the difference is formed or the slope of the extrapolated straight line G is determined; in this manner, the temperature T can be exactly determined by comparison with the calibration data according to FIG. 4 without the need that a shifting of the maximum of the absorption line B has to be measured.

FIGS. 1 to 4 show the basic functionality of the method according to the invention and demonstrate the execution in the laboratory. Since this involves an optical and noninvasive measuring method, the temperature measurement works in a comparable manner also within a body, for example the determination of the temperature of tissue, for example blood, inside a living body K.

For this purpose it is useful to mark the target area of the measurement by ultrasonic radiation. Such a method is described in a different context in DE 103 11 408 B3. The marking described therein of an area inside a body can be carried out in a corresponding manner for marking an area during temperature measurement. As an example, reference is made to FIG. 5. The infrared light of a laser 2 is projected in the described manner (for wavelengths $\lambda_1$ and $\lambda_2$) into the inside of a body K and the backscattered photons that represent the absorption are measured with a detector 6. The detector 6 not only registers the photons backscattered in the area of the blood vessel 11 but also a plurality of further photons that were scattered in other areas. A marking or selection can be accomplished by projection of ultrasonic radiation 13 by an ultrasonic radiation source 12 shown in FIG. 5. It is focused on the target area, namely the blood vessel 11. For example, in case of flowing blood, advantage can be taken, for example of the Doppler effect as this is described in DE 103 11 408 B3. The ultrasonic radiation source 12 generates pulsed ultrasonic radiation with a fixed pulse length and fixed repetition time. The evaluation unit, taking into account the pulse behavior, evaluates the light portion that actually contributes to the volume of the ultrasonic focus that can be extracted from the detector 6. Details are described in DE 103 11 408 B3 and DE 2006 036 920 that, however, are not concerned with the temperature determination but with the noninvasive measurement of the concentration of blood components. Beside, the method according to the invention can be combined with such a noninvasive measurement of the concentration of blood components. Therefore, the noninvasive measurement of the concentration of blood components, for example the measurement of the sugar content, can be accomplished, where at the same time, a temperature determination can also take place.

Since in practice the light portion marked by the ultrasonic sound potentially depends not only on the temperature of the monitored site but to a certain extent also on the gradient of the temperature on the surface and the site to be monitored, it can be useful to first carry out a reference measurement on the surface of the measured body, for example on the skin, where there too, a marking by ultrasonic focus can be useful. The measurement performed there depends solely on the temperature there and not on the temperature of potential intermediate positions or a temperature gradient so that subsequently a temperature measurement in the desired depth of the body can take place and, at the same time, a temperature differential measurement is carried out.

Finally, in addition to the correction it can be useful to carry out a correction measurement by an isosbestic wavelength. Details are not shown in the figures. Such an isosbestic wavelength is characterized in that the backscattered photon flux can only be influenced in the intermediate positions and at the monitored site and is completely independent of the (optical) absorption capacity of the water. Consequently, the scatter behavior can be "corrected out" of the performed measurement. In practice, the reference and correction measurements can take place in direct (temporal) relationship to the performed temperature measurement and can be considered immediately in the evaluation so that a device for carrying out the method according to the invention is quasi self-calibrating.

The invention claimed is:

1. A method of the noninvasive optical determination of the temperature of a flowing stream of blood within a body, the method comprising the step of:
    marking a site within the body through which the blood stream passes with pulsed ultrasonic radiation,
    irradiating the flowing blood stream at and around the site with two discrete wavelengths of infrared and/or visible light that are near the absorption line of the blood on two different sides of the absorption maximum defined by the absorption line whose position depends on the temperature of the blood, whereby the light is absorbed or backscattered to a degree dependent on proximity of the wavelength of the light to the absorption line,
    determining from that portion of the absorbed or backscattered light that is temporally related to the ultrasonic radiation respective absorption values for the two wavelengths,
    deriving at least one measured value dependent on the temperature or a measuring function dependent on the temperature from a ratio or a functional relation of these two determined absorption values to one another, and
    determining the temperature from the measured value or the measuring function by comparison with previously recorded calibration data.

2. The method according to claim 1, wherein the measured value is determined by determining the difference of the two absorption values lying on both sides of the maximum, or by determination of the slope of a straight line running through the measuring points.

3. The method according to claim 1 wherein the flowing blood stream is irradiated with infrared light or visible light with wavelengths between 600 nm and 2500 nm.

4. The method according to claim 3, wherein the measurement is carried out near the water absorption line at about 970 nm using, on the one hand, light of a first wavelength $\lambda_1$ between 950 and 970 nm and, on the other hand, light of a second wavelength $\lambda_2$ between 975 and 1000 nm.

5. The method according to claim 3, wherein the measurement is carried out near the water absorption line at about 1450 nm.

6. The method according to any claim 1 wherein the temperature of a medium on a body surface is determined.

7. The method according to claim 1, further comprising the steps, for determination of the temperature inside a body, of:
   first carrying out a reference measurement of the temperature on a surface of the body and
   subsequently determining the temperature out at the site inside the body.

8. The method according to claim 1, further comprising the step of, for determination of the temperature inside a body,
   carrying out a correction measurement with one or more isosbestic wavelengths, the flowing blood stream or the body being irradiated with light of an isosbestic wavelength at which the backscattered light portion is solely dependent on scatter effects inside the body and not on the absorption behavior of the flowing blood stream.

\* \* \* \* \*